US011324795B2

(12) United States Patent
Kim et al.

(10) Patent No.: US 11,324,795 B2
(45) Date of Patent: May 10, 2022

(54) **COMPOSITION COMPRISING *HORDEUM VULGARE* EXTRACT FOR PREVENTING OR TREATING SHORT STATURE**

(71) Applicant: UNIVERSITY-INDUSTRY COOPERATION GROUP OF KYUNG HEE UNIVERSITY, Gyeonggi-do (KR)

(72) Inventors: Hocheol Kim, Seoul (KR); Juyeon Park, Gyeonggi-do (KR); Sang Woug Park, Seoul (KR); Ji Young Kim, Gyeonggi-do (KR); Donghun Lee, Seoul (KR)

(73) Assignee: UNIVERSITY-INDUSTRY COOPERATION GROUP OF KYUNG HEE UNIVERSITY, Yongin-si (KR)

( * ) Notice: Subject to any disclaimer, the term of this patent is extended or adjusted under 35 U.S.C. 154(b) by 577 days.

(21) Appl. No.: 15/038,871

(22) PCT Filed: Nov. 24, 2014

(86) PCT No.: PCT/KR2014/011323
§ 371 (c)(1),
(2) Date: Jul. 25, 2016

(87) PCT Pub. No.: WO2015/076631
PCT Pub. Date: May 28, 2015

(65) Prior Publication Data
US 2016/0375085 A1    Dec. 29, 2016

(30) Foreign Application Priority Data

Nov. 25, 2013 (KR) .................. 10-2013-0143747

(51) Int. Cl.
| | | |
|---|---|---|
| *A61K 36/8998* | (2006.01) | |
| *A23L 33/105* | (2016.01) | |
| *A23K 10/30* | (2016.01) | |
| *A61K 47/10* | (2017.01) | |
| *A23L 2/52* | (2006.01) | |
| *A61K 9/00* | (2006.01) | |

(52) U.S. Cl.
CPC .......... *A61K 36/8998* (2013.01); *A23K 10/30* (2016.05); *A23L 2/52* (2013.01); *A23L 33/105* (2016.08); *A61K 9/0053* (2013.01); *A61K 9/0095* (2013.01); *A61K 47/10* (2013.01); *A23V 2002/00* (2013.01); *A61K 2236/00* (2013.01); *A61K 2236/331* (2013.01); *A61K 2236/333* (2013.01)

(58) Field of Classification Search
CPC ................................................ A61K 36/8998
See application file for complete search history.

(56) References Cited

U.S. PATENT DOCUMENTS

2010/0316741 A1    12/2010    Kim et al. .................... 424/728

FOREIGN PATENT DOCUMENTS

| JP | 63-119655 | 5/1988 | | |
|---|---|---|---|---|
| JP | 02-234616 | 9/1990 | | |
| JP | 2007-84503 | 4/2007 | | |
| KR | 10-2004-0062296 | 7/2004 | | |
| KR | 10-2005-0041272 | 5/2005 | | |
| KR | 10-0673266 | 1/2007 | | |
| KR | 10-0715653 | 5/2007 | | |
| KR | 10-2009-0017935 | 2/2009 | | |
| KR | 10-2010-0090514 | 8/2010 | | |
| KR | 20110045291 A | * | 5/2011 | |
| WO | WO-2009041515 A1 | * | 4/2009 | ........... A23L 33/105 |

OTHER PUBLICATIONS

"Mayo Clinic: Down Syndrome". Internet publication date: Mar. 18, 2018. [Retrieved from the Internet on: Mar. 31, 2020], Retrieved from: <URL: https://www.mayoclinic.org/diseases-conditions/down-syndrome/symptoms-causes/syc-20355977>. (Year: 2018).*
"Health conditions: Prader-Willi syndrome" Internet publication date: Mar. 17, 2020. [Retrieved from the Internet on: Mar. 30, 2020], Retrieved from: <URL: https://ghr.nlm.nih.gov/condition/prader-willi-syndrome>. (Year: 2020).*
"Children's National: Pediatric Short Stature". Retrieved from the Interneton: Mar. 30, 2020. Retrieved from the Internet: < https://childrensnational.org/visit/conditions-and-treatments/diabetes-hormonal-disorders/short-stature> (Year: 2020).*
Letter/Written Disclosure of the Information Disclosure Statement for the above-referenced application, filed herewith on Sep. 8, 2016, 2 pages.
Huh and Park, "Questionnaire-based analysis of growth-promoting attempts among children visiting a university growth clinic," Korean J. Pediatr. 52(5):576-580 (2009) [Article in Korean with English language abstract].
Isgaard et al., "Effects of local administration of GH and IGF-1 on longitudinal bone growth in rats," Am. J. Physiol. 250(4 Pt 1):E367-372 (1986).
Kang et al., "Economic evaluation of a weekly administration of a sustained-release injection of recombinant human growth hormone for the treatment of children with growth hormone deficiency." Korean J. Pediatr. 52(11):1249-1259 (2009) [Article in Korean with English language Abstract].
Lee and Han, "Effects of growth hormone therapy in children with idiopathic short stature," Korean J. Pediatr. 48(8):865-870 (2005) [Article in Korean with English language abstract].
Machine English translation of Pub. No. KR 10-0673266 (App. No. 10-2006-0035973), published Jan. 24, 2007, Korean Intellectual Property Office, 18 pages.

(Continued)

*Primary Examiner* — Amy L Clark
(74) *Attorney, Agent, or Firm* — Potomac Law Group, PLLC

(57) ABSTRACT

Disclosed is a composition, which comprises *Hordeum vulgare* extract as an active ingredient and is effective at promoting longitudinal bone growth.

7 Claims, 1 Drawing Sheet

(56) References Cited

OTHER PUBLICATIONS

Machine English translation of Pub. No. KR 10-0715653 (App. No. 10-2006-0035972), published May 9, 2007, Korean Intellectual Property Office, 18 pages.
Machine English translation of Pub. No. KR 10-2004-0062296 (App. No. 10-2003-0000099), published Jul. 7, 2004, Korean Intellectual Property Office, 9 pages.
Machine English translation of Pub. No. KR 10-2005-0041272 (App. No. 10-2003-0076392), published May 4, 2005, Korean Intellectual Property Office, 20 pages.
Machine English translation of Pub. No. KR 10-2009-0017935 (App. No. 10-2007-0082464), published Feb. 19, 2009, Korean Intellectual Property Office, 9 pages.
Raben, M.S., "Treatment of a pituitary dwarf with human growth hormone," J. Clin Endocrinol. Metab. 18(8):901-903 (1958).
Shin, C. H., "Current use of growth hormone in children," Korean J. Pediatr. 49(7):703-709 (2006) [Article in Korean with English language abstract].
International Search Report and Written Opinion, dated Feb. 23, 2015, in connection with AS International Patent Application No. PCT/KR2014/011323 [English translation and original document in Korean], 22 pages.
Letter/Written Disclosure of the Supplemental Information Disclosure Statement for the abovereferenced application, filed herewith on Jun. 27, 2017, 2 pages.
Machine-generated English translation of Publication No. JP02-234616, retrieved Jun. 9, 2017, The Japan Platform for Patent Information (J-PlatPat), 3 pages.
Machine-generated English translation of Publication No. JP63-119655, retrieved Jun. 9, 2017, The Japan Platform for Patent Information (J-PlatPat), 4 pages.
Machine-generated English translation of Publication No. JP 2007-84503, retrieved Jun. 9, 2017, The Japan Platform for Patent Information (J-PlatPat), 13 pages.
International Preliminary Report on Patentability, dated May 31, 2016, in connection with International Patent Application No. PCT/KR2014/011323 [English translation and original document in Korean], 17 pages.
Office Action, dated Jun. 6, 2017, in connection with Japenese Patent Application No. 2016-534216 [English translation and original document in Japanese], 11 pages.
Masafumi, S., "Basic Course for Drug Development XI Pharmaceutical Manufacturing Method," 1:15-16, Chijinshokan Co., Ltd, Japan (1971).
Letter/Written Disclosure of the Supplemental Information Disclosure Statement for the abovereferenced application, filed herewith on Sep. 15, 2016, 2 pages.
Park et al., "Effect of Hwalhylsungjang-san and KC101 Composed of Oriental Medicinal Stuffs on Physical Development in Growing Rats," J. Korean Oriental Med., 24(1):1-8 (2003) [Article in Korean with English language abstract].
Partial English Translation of Korean Publication No. 10-0673266, 4 pages.
Partial EnglishTranslation of Korean Publication No. 10-0715653, 4 pages.
Partial English Translation of Korean Publication No. 10-2004-0062296, 2 pages.
Partial English Translation of Korean Publication No. 10-2005-0041272, 3 pages.
Partial English Translation of Korean Publication No. 10-2009-0017935, 3 pages.
Partial English Translation of Korean Publication No. 10-2010-0090514, 3 pages.

* cited by examiner

Control  rhGH  *Hordeum vulgare* 30

COMPOSITION COMPRISING *HORDEUM VULGARE* EXTRACT FOR PREVENTING OR TREATING SHORT STATURE

RELATED APPLICATIONS

This application is the U.S. National Stage of International Application. No. PCT/KR2014/011323, filed 24 Nov. 2014, which claims benefit of priority to Korean Patent Application KR 10-2013-0143747, filed 25 Nov. 2013, the specification of which is incorporated by reference herein.

TECHNICAL FIELD

The present invention relates to a composition for promoting longitudinal bone growth, comprising *Hordeum vulgare* extract as an active ingredient. More particularly, the present invention relates to a pharmaceutical composition for preventing or treating growth disorder, a food composition for preventing or ameliorating growth disorder, and a feed composition, each of which comprises *Hordeum vulgare* extract as an active ingredient.

BACKGROUND ART

Short stature means the case where the height is less than 3% (the third from the shortest among 100 children) in a normal height distribution of children of the same age and gender. Such short stature is classified into, depending on its cause, normal variant short stature due to genetic predisposition and constitutionally short predisposition, without any disease, and secondary short stature due to disease.

Normal variant short stature may be further classified into familial short stature, constitutional growth delay, and idiopathic short stature. Familial short stature corresponds to the case where the height is genetically low, and constitutional growth delay is the case where growth is constitutionally late and the current height is low but growth continues until late age due to late puberty and thus the final adult height reaches the normal range. Finally, idiopathic short stature may be defined as children who have short stature, with a height shorter than −2 standard deviations (SD) from the mean height or below the third percentile, have no special cause for short stature, are born with normal birth weights, have normal limb-to-trunk length ratios, intake adequate nutrition, have no psychosocial problems, and secrete growth hormones normally (Shin et al., Current use of growth hormone in children, Korean J Ped. Vol. 49. No. 7. 2006).

On the other hand, secondary short stature due to disease may include primary growth disorder (endogenous disorder) and secondary growth disorder (exogenous growth disorder). Examples of the primary growth disorder may include osteochondrodysplasia, short stature due to chromosomal abnormalities (Down Syndrome or Turner Syndrome), small for gestational age (intrauterine growth retardation), short stature due to Prader-Willi Syndrome, short stature due to Russell-Silver Syndrome, and short stature due to Noonan Syndrome. Also, examples of the secondary growth disorder may include short stature due to malnutrition, short stature due to chronic systemic diseases, short stature due to growth hormone deficiency, short stature due to hypothyroidism, short stature due to precocious puberty, short stature due to Cushing's Syndrome, and psychosocial dwarfism.

Most children who visit hospitals due to short stature fall under normal variant short stature. Foreign studies reported that among causes of patients with short stature, familial and constitutional short stature account for 80% thereof, growth hormone deficiency accounts for 10%, thyroid dysfunction accounts for 4%, chronic diseases such as chronic renal failure or the like account for 3%, chromosomal abnormalities account for 1%, skeletal dysplasia accounts for 1%, and mental illness accounts for 1% thereof (Establishment of function evaluation system related to growth regulation, 2003).

A growth hormone agent, which is mainly used for the treatment of short stature, was initially applied only to children with short stature due to growth hormone deficiency, but the application range thereof has widened to short stature due to Turner Syndrome and chronic renal failure, and adult growth hormone deficiency. In a recent FDA report, the therapeutic indications thereof have expanded to children who have difficulty catching up in growth, including those small for gestational age, afflicted with Prader-Willi Syndrome, and idiopathic short stature with a height below −2.25 SD (Lee Kyong-A et al., Effects of growth hormone therapy in children with idiopathic short stature. 2005, Raben M S. Treatment of a pituitary dwarf with human growth hormone. 1958). The therapeutic indications of recombinant human growth hormone for idiopathic short stature in children were newly approved in August, 2009 by the Korea Food and Drug Administration.

In particular, many children with idiopathic short stature have been observed to exhibit a height increase within 1 to 2 years after the use of growth hormone, but whether the final adult height was increased is difficult to check. Based on comprehensive reports by Cochrane on the effects of growth hormone therapy, the growth rate is increased by about 2.86 cm on the first year in which the growth hormone is used compared to when the growth hormone is not used, and the final adult height is increased by 4 to 6 cm upon the use of growth hormone for an average of 5.3 years. The increase in the final adult height is greater with an increase in the amount of the growth hormone, and the use of growth hormone is continuously required in order to reach the final adult height, and there is no consistent conclusion as to whether children with short stature may gain psychological benefits after growth hormone therapy (Shin et al., Current use of growth hormone in children, Korean J Ped. Vol. 49. No. 7. 2006). Furthermore, the administration of growth hormone to idiopathic short stature is ethically problematic because a therapeutic agent is used on children without any disease, and also has drawbacks, including the use of a large amount thereof and a high price, amounting to 35,000 dollars to increase the final adult height by 2.5 cm. With longer treatment periods, the growth effect is decreased, and thus the amount of growth hormone that is added has to be increased. When the use of growth hormone is stopped, the growth rate is temporarily further reduced, and also, the therapeutic effect is different for each person, and no indicator that can predict a good response effect has been suggested. Moreover, it is difficult to determine the use of growth hormone under the condition that there are no results of long-term observation to detect problems which may occur upon long-term use of growth hormone in large amounts (Shin et al., Current use of growth hormone in children, Korean J Ped. Vol. 49. No. 7. 2006).

Meanwhile, a conventional growth hormone injection agent is subcutaneously injected 6 to 7 times a week every night before sleeping at home. Growing children who are injected daily undergo physical pain and psychological pressure and caregivers who perform inoculation on their children suffer from complications and a psychological burden. Also, refrigerated storage and transport of the injection agent are difficult when traveling or taking long trips, and there is psychological pressure to conceal such inoculation from those outside the family (Kang et al., Economic evaluation of a sustained-release injection of growth hormone for the treatment of children with growth hormone deficiency. 2009). Based on the results of a questionnaire survey of caregivers of child patients who are currently injected daily, the utility weight for the quality of life of child patients who are injected daily is an average of 0.584 (the 0 to 100 response scale being converted to a 0 to 1 score scale), corresponding to 58.4% of normal healthy status (a score of 100). The quality of life that is expected upon injection once a week is an average of 0.784, corresponding to 78.4% of normal healthy status (Kang Hye-Young et al., Economic evaluation of a sustained-release injection of growth hormone for the treatment of children with growth hormone deficiency. 2009). Generally, 3% of children who are administered with growth hormone are known to exhibit side effects. Such children may suffer from arthralgia or myalgia, but the frequency of occurrence thereof is low compared to adults, and fat atrophy may occur around the injected region, and gynecomastia may temporarily occur. Furthermore, there may occur changes in hormones, including thyroid hormones, and metabolites, and thus thyroid function tests have to be performed at intervals of 3 to 6 months, and moreover, facial asymmetry is aggravated in some patients who are small for gestational age. Increased intracranial pressure may be frequently caused in children, especially patients with Turner Syndrome, chronic renal failure and organic growth hormone deficiency, but is ameliorated upon stoppage of administration of the growth hormone and may partially relapse upon reuse of the growth hormone (Shin et al., Current use of growth hormone in children, Korean J Ped. Vol. 49. No. 7. 2006).

Based on [Long-term epidemiological studies with somatropin formulation administered to child patients] published in France according to the European Medicines Agency (EMA) and the Food and Drug Administration (FDA), USA, the risk of increasing the death rate of children due to the use of a childhood growth failure therapeutic agent "somatropin formulation" has begun to be reviewed. As the result of analysis of about 7,000 youths to which the same formulation was administered throughout France, the death rate of patients using "somatropin formulation" was about 30% higher than that of general persons (the entire population of France), and the risk of death rate was increased due to doses exceeding permitted amounts (Korea Food and Drug Administration, 2010).

In Korea's population distribution according to age, as of 2009, the number of people 5 to 14 years old who receive the growth treatment is approximately six million, among which the number of people with short stature is approximately 180,000 persons, accounting for 3% thereof. The number of insured persons in 2009 was 36,000 persons, corresponding to about 20% thereof, and the total number of people receiving insurance benefits for growth hormone therapy to treat short stature according to the Health Insurance Review & Assessment Service was 12,012 persons in 2009, and thus 24,000 persons, about 66.6%, of patients with short stature as the insured persons, do not receive treatment of short stature. The reason why a large number of patients with short stature do not receive such treatment is as follows: even when patients with short stature are subjected to growth hormone therapy through insurance coverage, costs amounting to 2,500,000 to 3,000,000 won per year are incurred, and furthermore, idiopathic short stature, which constitutes about 80% of short stature cases, is not covered by insurance, undesirably incurring high costs of 10,000,000 to 15,000,000 won per year and physical pain and psychological burdens on children who are injected daily.

Although growth hormone therapy has been proven to have a superior growth effect compared to other medical methods, satisfaction therewith is only 29.1% due to various factors, including cost, convenience, etc. (Huh Kyoung, Park Mi-Jung, Questionnaire-based analysis of growth-promoting attempts among children visiting a university growth clinic, Korean Journal of Pediatrics Vol. 52, No. 5, 2009). The global market potential for oral products of therapeutic agents for short stature is estimated to be at least 5 billion dollars (Hanall Biopharma, Corporate presentation, 2009).

Meanwhile, Chinese medicines are highly preferred for medical treatment and health promotion in Asian cultures. Based on survey results of parents who have visited growth clinics, the number of cases where growth-promoting Chinese medicines are taken to increase the height of children is 13 times the number of cases where growth hormone therapy is performed, and the acceptance of Chinese medicines is very high compared to the growth hormone. According to the survey results of parents of 823 children (416 male children and 407 female children) who visited the growth clinic of Inje University Sanggye Paik Hospital from 2006 to 2007, the proportion of cases where artificial treatment is performed to increase the height is 33.4%, among which the cases where growth-promoting Chinese medicines are administered by Chinese clinics account for 37.8% thereof, the cases where supplements for increasing height are taken account for 37.1%, the cases involving exercise/fitness equipment therapy account for 3.0%, and the cases where growth hormone therapy is performed account for 2.9% (Huh Kyoung, Park Mi-Jung, Questionnaire-based analysis of growth-promoting attempts among children visiting a university growth clinic, Korean Journal of Pediatrics Vol. 52, No. 5, 2009). Most prescriptions used for clinical Chinese medicines have not yet revealed their efficacy in growth models and the pharmacokinetic and pharmacodynamic indices thereof are lacking. For clinically available Chinese medicines, there is a need to scientifically demonstrate the efficacy thereof in growth models through animal testing and to develop materials having high efficacy. According to the results of a survey of parents of 823 children who visited a growth clinic, the satisfaction with growth therapy is the highest, at 29.1%, for growth hormone therapy, 6.6% for exercise/fitness equipment therapy, 6.2% for Chinese medicines, and the lowest, 2.8%, for growth supplements. The growth hormone injection agent shows very high satisfaction compared to the other methods, and the growth effect thereof has been proven to be excellent under medical studies, but satisfaction therewith is only 29.1% attributable to various factors, such as cost, convenience, etc. (Huh Kyoung, Park Mi-Jung, Questionnaire-based analysis of growth-promoting attempts among children visiting a university growth clinic, Korean Journal of Pediatrics Vol. 52, No. 5, 2009).

Hence, there is required the development of formulations derived from natural materials, which may be orally administered, are highly effective at treating short stature, and have no side effects.

*Hordeum vulgare* is a medicinal material obtained by drying leaves of barley (*Hordeum vulgare* L.) of Gramineae and then gently roasting them. Amylase is produced as a malt enzyme and is also referred to barley malt and used to brew beer. In the field of Chinese medicine, it has been used to treat digestive disorders caused by weakness of the spleen and stomach, indigestion and lack of lactation.

The present inventors have studied promising candidates for short stature therapeutic agents derived from natural materials, and have ascertained that when the *Hordeum vulgare* extract is orally administered at a low concentration (30 mg/kg), a superior longitudinal bone growth effect may be exhibited compared to growth hormone therapy, thus culminating in the present invention.

DISCLOSURE

Technical Problem

An object of the present invention is to provide a pharmaceutical composition for the prevention or treatment of growth disorder, comprising *Hordeum vulgare* extract as an active ingredient.

Another object of the present invention is to provide a food composition for the prevention or amelioration of growth disorder, comprising *Hordeum vulgare* extract as an active ingredient.

Still another object of the present invention is to provide a feed composition, comprising *Hordeum vulgare* extract as an active ingredient.

Yet another object of the present invention is to provide use of comprising *Hordeum vulgare* extract for preparation of a medicament for treating growth disorder.

Still yet another object of the present invention is to provide a method of preventing or treating growth disorder, including administering a composition comprising *Hordeum vulgare* extract as an active ingredient.

Technical Solution

In order to accomplish the above objects, the present invention provides a pharmaceutical composition, a food composition, and a feed composition, each of which comprises *Hordeum vulgare* extract as an active ingredient. Individual compositions are described below.

Pharmaceutical Composition

The present invention addresses a pharmaceutical composition for preventing or treating a growth disorder, comprising *Hordeum vulgare* extract as an active ingredient.

The *Hordeum vulgare* extract may be extracted in water, an alcohol, or a mixture thereof. The alcohol is preferably a C1-C4 lower alcohol, and more preferably includes methanol or ethanol. The extraction process may include, but is not limited to, shaking extraction, Soxhlet extraction, or reflux extraction. The extraction temperature is preferably 40 to 100° C., and more preferably 60 to 80° C. Also, the extraction time is preferably 2 to 24 hr, and the extraction process is preferably performed 1 to 5 times.

The pharmaceutical composition of the present invention comprising the *Hordeum vulgare* extract may exhibit superior longitudinal bone growth effects, as is apparent from Table 1 and FIGS. 1 and 2, compared to when using growth hormone as a conventional therapeutic agent, and may thus be used for the prevention or treatment of growth disorder.

Despite oral administration (p.o.), the pharmaceutical composition of the present invention may show significant effects at a low concentration (30 mg/kg), thereby decreasing the pharmaceutical burden in which the *Hordeum vulgare* extract has to be contained in a large amount, and thus, this composition may be used as an oral therapeutic agent.

Furthermore, the pharmaceutical composition of the present invention contains an herbal component as the active ingredient, and is thus effective at preventing or treating the growth disorder without the side effects of a conventional growth hormone agent.

Meanwhile, the growth disorder may include normal variant short stature or secondary short stature due to disease. The normal variant short stature may include familial short stature, constitutional growth delay, or idiopathic short stature in a narrow sense. Also, the secondary short stature due to disease may include primary growth disorder (endogenous disorder) or secondary growth disorder (exogenous growth disorder). Examples of the primary growth disorder may include osteochondrodysplasia, short stature due to chromosomal abnormalities (Down Syndrome or Turner Syndrome), small for gestational age (intrauterine growth retardation), short stature due to Prader-Willi Syndrome, short stature due to Russell-Silver Syndrome, and short stature due to Noonan Syndrome, and examples of the secondary growth disorder may include short stature due to chronic systemic diseases, short stature due to growth hormone deficiency, short stature due to hypothyroidism, short stature due to precocious puberty, short stature due to Cushing's Syndrome, and psychosocial dwarfism.

In the present invention, the *Hordeum vulgare* extract is preferably contained in an amount of 0.1 to 50 wt % based on the total weight of the pharmaceutical composition of the present invention. However, the above amount range is not necessarily limited thereto and may vary depending on the patient's status, the kind of disease, and the extent of progression of disease.

In the pharmaceutical composition of the present invention, the *Hordeum vulgare* extract may be administered once or divided into multiple administrations several times per day in an amount of about 1 mg to 1 g, preferably 10 mg to 150 mg, and more preferably 20 mg to 50 mg for an adult. However, the amount of the *Hordeum vulgare* extract that is administered may be appropriately adjusted depending on the patient's status, such as severity of condition, age, gender, weight and the like, dosage form of drug, and administration route and period.

Since the pharmaceutical composition of the present invention has neither toxicity nor side effects, it may be safely used even upon long-term administration.

The pharmaceutical composition of the present invention may include pharmaceutically acceptable additives, such as a diluent, a binder, a disintegrant, a lubricant, a pH controller, an antioxidant, a solution adjuvant, etc., within the range that does not impair the effects of the present invention.

The diluent may include sugar, starch, microcrystalline cellulose, lactose (lactose hydrate), glucose, D-mannitol, alginate, alkaline earth metal salts, clay, polyethylene glycol, anhydrous calcium hydrogen phosphate, or mixtures thereof.

The binder may include starch, microcrystalline cellulose, highly dispersible silica, mannitol, D-mannitol, sucrose, lactose hydrate, polyethylene glycol, polyvinylpyrrolidone (povidone), a polyvinylpyrrolidone copolymer (copovidone), hypromellose, hydroxypropylcellulose, natural gum, synthetic gum, copovidone, gelatin, or mixtures thereof.

The disintegrant may include starch or modified starch, such as sodium starch glycolate, corn starch, potato starch, or pregelatinized starch; clay, such as bentonite, montmorillonite, or veegum; cellulose, such as microcrystalline cellulose, hydroxypropyl cellulose, or carboxymethyl cellulose; algin, such as sodium alginate or alginic acid; crosslinked cellulose, such as croscarmellose sodium; gum, such as guar gum or xanthan gum; a crosslinked polymer, such as crosslinked polyvinylpyrrolidone (crospovidone); an effervescent agent, such as sodium bicarbonate or citric acid; or mixtures thereof.

The lubricant may include talc, stearic acid, magnesium stearate, calcium stearate, sodium lauryl sulfate, hydrogenated vegetable oil, sodium benzoate, sodium stearyl fumarate, glyceryl behenate, glyceryl monooleate, glyceryl monostearate, glyceryl palmitostearate, colloidal silicon dioxide, or mixtures thereof.

The pH controller may include an acidifying agent, such as acetic acid, adipic acid, ascorbic acid, sodium ascorbate, sodium etherate, malic acid, succinic acid, tartaric acid, fumaric acid, or citric acid, and an alkalizing agent, such as precipitated calcium carbonate, aqueous ammonia, meglumine, sodium carbonate, magnesium oxide, magnesium carbonate, sodium citrate, or tribasic calcium phosphate.

The antioxidant may include dibutyl hydroxy toluene, butylated hydroxyanisole, tocopherol acetate, tocopherol, propyl galate, sodium bisulfite, sodium pyrosulfite, etc. The solution adjuvant may include sodium lauryl sulfate, polyoxyethylene sorbitan fatty acid ester such as polysorbate, docusate sodium, poloxamer, etc.

For oral administration, the pharmaceutical composition of the present invention may be provided in the form of a solid formulation such as a tablet, a pill, a powder, a granule, or a capsule, and such a solid formulation may be prepared by mixing the *Hordeum vulgare* extract with at least one excipient, for example, starch, calcium carbonate, sucrose or lactose, or gelatin. In addition to the simple excipient, useful is a lubricant such as magnesium stearate or talc. Alternatively, the pharmaceutical composition for oral administration may be provided in the form of a liquid formulation, such as a suspension, an oral solution, an emulsion, or a syrup, and may be prepared into a liquid formulation using not only water and liquid paraffin but also various excipients, for example, a humectant, a sweetener, a fragrance, a preservative and the like.

For parenteral administration, the pharmaceutical composition of the present invention may be provided in the form of a formulation including a sterile aqueous solution, a non-aqueous solution, a suspension, an emulsion, a lyophilisate, or a suppository.

The non-aqueous solution or suspension may include propylene glycol, polyethylene glycol, a vegetable oil such as olive oil, and an injectable ester such as ethyl oleate. The substrate for a suppository may include Witepsol, Macrogol, Tween 61, cacao oil, laurin oil, glycerogelatin, etc.

As used herein, the term "administration" refers to the introduction of the pharmaceutical composition of the present invention to a patient through any proper method. As the administration route of the pharmaceutical composition of the invention, any typical route may be applied without limitation so long as it reaches the tissue of interest. Specific examples thereof may include, but are not limited to, oral administration, intraperitoneal administration, intravenous administration, intramuscular administration, subcutaneous administration, intradermal administration, intranasal administration, intrapulmonary administration, intrarectal administration, intravitreal administration, intraperitoneal administration, and intrathecal administration. For example, administration may be carried out by oral, rectal, venous, muscular, subcutaneous, intrauterine epidural or intracerebroventricular injection.

Also, the pharmaceutical composition of the present invention may further include an additional active ingredient having an effect of treating growth disorder.

The pharmaceutical composition according to the present invention may be used alone or in combination with any other method, such as hormone therapy or drug therapy, in order to prevent or treat growth disorder.

Food Composition

The present invention addresses a food composition for the prevention or amelioration of growth disorder, comprising *Hordeum vulgare* extract as an active ingredient.

The *Hordeum vulgare* extract may be prepared in the same manner as in the pharmaceutical composition.

The food composition of the present invention may include *Hordeum vulgare* extract alone, or may further include an additive that is typically used for any other food composition, functional health food or drink.

For example, the food composition of the present invention may contain a sweetener, such as white sugar, crystalline fructose, glucose, D-sorbitol, mannitol, isomalto-oligosaccharide, stevioside, aspartame, acesulfame potassium, sucralose, etc., an acidulant, such as anhydrous citric acid, DL-malic acid, succinic acid and salts thereof, a preservative such as benzoic acid and derivatives thereof, various nutrients, vitamins, minerals (electrolytes), a flavor such as a synthetic flavor and a natural flavor, a colorant, an enhancer (cheese, chocolate, etc.), pectic acid and salts thereof, alginic acid and salts thereof, an organic acid, a protective colloid thickener, a pH controller, a stabilizer, an antiseptic, glycerin, alcohol, and a carbonating agent for use in carbonated drinks. Furthermore, the food composition of the present invention may contain flesh for the preparation of natural fruit juice and vegetable drinks. The amounts of the additives may fall in the range of about 20 parts by weight or less based on 100 parts by weight of the food composition of the present invention.

When the food composition of the present invention is a drink, it may further include a flavoring agent or a natural carbohydrate typically useful in drinks. The natural carbohydrate may include monosaccharides such as glucose or fructose, disaccharides such as maltose or sucrose, polysaccharides such as dextrin or cyclodextrin, or sugar alcohols such as xylitol, sorbitol or erythritol. Furthermore, the flavoring agent may include a natural flavoring agent such as thaumatin or a *stevia* extract (Rebaudioside A, Glycyrrhizin, etc.) or a synthetic flavoring agent such as saccharin, aspartame, etc. When the food composition is a drink, the natural carbohydrate is typically contained in an amount of about 1 to 20 g, and preferably about 5 to 12 g, based on 100 mL of the composition.

The food composition of the present invention may be prepared in the form of a powder, a granule, a tablet, a capsule, or a drink, and may thus be used as a food, a drink, a gum, a tea, a vitamin complex, or a health supplement.

Also, the food composition of the present invention may be added to a drug, a food and a drink to prevent or ameliorate the growth disorder. For example, the food composition of the present invention may be added to a food, a drink, a gum, a tea, a vitamin complex, a health supplement and the like.

The food composition of the present invention may be added to a food or a drink to prevent or ameliorate the growth disorder. The composition of the present invention may be added in an amount of 1 to 5 wt % based on the total weight of the food, and may be added in an amount of 0.02 g to 10 g, and preferably 0.3 g to 1 g, based on 100 mL of the drink.

Feed Composition

The present invention addresses a feed composition comprising *Hordeum vulgare* extract as an active ingredient. The

*Hordeum vulgare* extract may be prepared in the same manner as in the pharmaceutical composition.

In the present invention, the *Hordeum vulgare* extract exhibits a longitudinal bone growth effect and may thus be contained as an animal growth promoter in the feed composition.

Specifically, feed according to the present invention comprising the *Hordeum vulgare* extract as an active ingredient may be provided in various feed forms known in the art, preferably including concentrated feed, roughage, and/or special feed.

The concentrated feed may include seed fruits including grains such as wheat, oats, corn, etc.; bran such as rice bran, wheat bran, barley bran, etc., which are byproducts from refining grains; dregs, which are byproducts from extracting oil from soybeans, canola, sesame, flaxseed, coconut palm, etc.; residue such as residual starch substances, which are the main component of starch residue that remains after removing starch from sweet potatoes, potatoes, etc.; fish soluble which is a concentrate of fresh liquid obtained from fish meal, fish waste, and fish; animal-based feed such as meat meal, blood meal, feather meal, powdered skim milk, dried whey, obtained from drying whey, which is a residue from producing cheese from milk or casein from skim milk, etc.; yeasts, *chlorella*, seaweeds, etc.

The roughage may include fresh grass feed such as wild grass, herbage, green manure, etc.; root vegetables such as turnips for feed, beets for feed, rutabagas, which are a type of turnip, etc; silage, which is a storage feed obtained by placing fresh grass, green manure, paper mulberries, etc., in a silo and performing lactic acid fermentation; dried grass obtained by cutting and drying wild grass and herbage, straw of crops for breeding stock; and leaves of beans and other plants.

The special feed may include mineral feed such as oyster shells, halite, etc.; urea feed such as urea or its derivatives, diureide isobutene, etc.; and feed additives or dietary supplements, which are added in small amounts to a mixed feed in order to supplement ingredients which may be lacking when only mixing natural feed ingredients or to increase the shelf life of feed.

The feed composition according to the present invention may include various feed additives.

As used herein, the term "feed additive" refers to a material that is added to supplement nutrients, prevent a reduction in weight, increase the digestion availability of cellulose in the feed, improve milk quality, prevent reproductive disorders, increase pregnancy rate, and prevent heat stress in summer. The feed additive according to the present invention corresponds to a supplementary feed under control of the Livestock and Fish Feed Act, and may further include a mineral premix, such as sodium bicarbonate (baking soda), bentonite, magnesium oxide, a composite mineral, etc., a trace mineral, such as zinc, copper, cobalt, selenium, etc., a vitamin, such as carotene, vitamin E, vitamin A, D, E, nicotinic acid, a vitamin B complex, etc., a protective amino acid agent, such as methionine, lysine, etc., a protective fatty acid agent, such as a fatty acid calcium salt, etc., live bacteria, such as probiotics (*Lactobacillus*), a yeast culture, a mold fermentation, etc., a yeast and the like.

In the present invention, the feed composition may be applied to individuals without particular limitation so long as such individuals are targeted for longitudinal bone growth. The individuals may include animals, for example, mammals, such as non-primates (e.g. cattle, pigs, horses, cats, dogs, rats, and mice) and primates (e.g. monkeys, for example, cynomolgous monkeys and chimpanzees). In another embodiment, the individuals may include livestock animals (e.g. horses, cattle, pigs, etc.) or pets (e.g. dogs or cats).

In the present invention, the amount of the feed composition that is added may vary depending on the animal's species, size, weight, and age. The typical amount thereof may range from 0.001 to 10 g animal/day. The present invention is not limited thereto.

Method of Preventing, Ameliorating or Treating Growth Disorder

The present invention addresses a method of preventing, ameliorating or treating growth disorder, including administering the pharmaceutical composition, the food composition or the feed composition to a subject in need thereof. In the present invention, the subject includes a mammal, especially a human.

In the present invention, the growth disorder may include normal variant short stature or secondary short stature due to disease. The normal variant short stature may include familial short stature, constitutional growth delay, or idiopathic short stature in a narrow sense. The secondary short stature due to disease may include primary growth disorder (endogenous disorder) or secondary growth disorder (exogenous growth disorder). Examples of the primary growth disorder may include osteochondrodysplasia, short stature due to chromosomal abnormalities (Down Syndrome or Turner Syndrome), small for gestational age (intrauterine growth retardation), short stature due to Prader-Willi Syndrome, short stature due to Russell-Silver Syndrome, and short stature due to Noonan Syndrome, and examples of the secondary growth disorder may include short stature due to chronic systemic diseases, short stature due to growth hormone deficiency, short stature due to hypothyroidism, short stature due to precocious puberty, short stature due to Cushing's Syndrome, and psychosocial dwarfism.

Advantageous Effects

According to the present invention, *Hordeum vulgare* extract can exhibit superior longitudinal bone growth effects even upon oral administration (p.o.) at low concentration, compared to when using a growth hormone as a conventional therapeutic agent. Therefore, a pharmaceutical composition and a food composition according to the present invention are effective at preventing, ameliorating or treating growth disorder, and a feed composition of the present invention can effectively promote the longitudinal bone growth of an animal.

MODE FOR INVENTION

A better understanding of the present invention may be obtained through the following example and experimental example, which are set forth to illustrate, but are not to be construed as limiting the scope of the present invention.

Example 1

Preparation of *Hordeum vulgare* (*H. vulgare*) Extract

*Hordeum vulgare* was purchased from Yaksudang, and used after having been validated by the Dept. of Herbal Pharmacology, College of Oriental Medicine, Kyung Hee University. In order to prepare the *Hordeum vulgare* extract, 1 L of 70% ethanol was added to 100 g of *Hordeum vulgare*, reflux extracted at 80° C. for 3 hours, and then filtered with filter paper. The resulting extract liquid was concentrated under reduced pressure and then lyophilized, thus obtaining 13.47 g (yield 13.5%) of the *Hordeum vulgare* extract.

Experimental Example 1

Evaluation of Longitudinal Bone Growth Effect of *Hordeum vulgare* Extract—Tetracycline Staining Method <1-1> Preparation of Experimental Animals As experimental animals, four-week-old Sprague-Dawley female rats (Samtako, Korea) weighing about 100 g were purchased and cared for so as to be acclimatized to the experimental environment while supplying sufficient feed and water. After about 1 week for the acclimatization period, animal testing was performed.

<1-2> Evaluation of Longitudinal Bone Growth Effect

Figure 1:
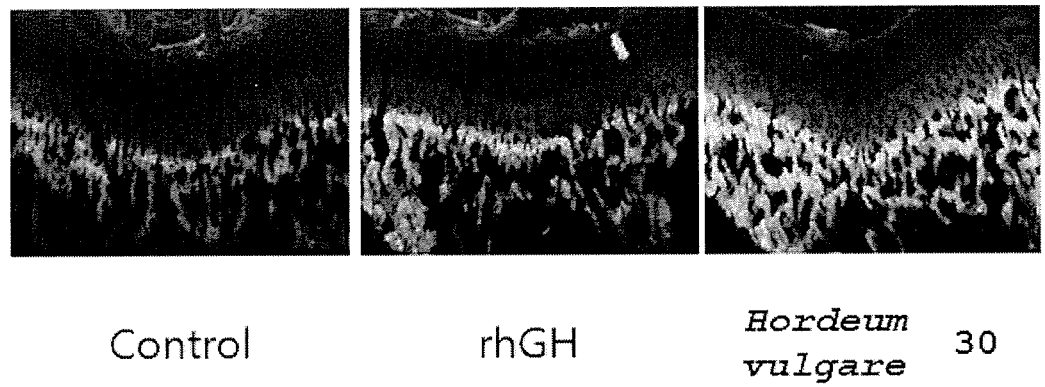
FIG. 1 illustrates the fluorescence microscope images of luminescence generated from the deposited tibial epiphyseal growth plate after injection of tetracycline to rats.

Two days after administration, 20 mg/kg of tetracycline hydrochloride (Sigma T7660) was injected intraperitoneally to all test groups. Two days thereafter, the rats were sacrificed via cervical dislocation, after which the left and right tibiae were removed, fixed in a fixing solution at 4° C. for 3 days, allowed to stand in 50 mM EDTA for 1 day, demineralized, and immersed in 30% sucrose overnight to protect freezing. The bone tissue thus dehydrated was frozen, and cut into 40 μm sections using a sliding microtome (HM440E, Zeiss, Germany), thus collecting sagittal sections of the proximal part of the tibia. To measure the bone growth, each sagittal section of the proximal part of the tibia, 40 μm thick, was placed on a slide glass, dried, and then observed under UV light at a wavelength of 400 nm using a fluorescence microscope (FIG. 1). Using image analysis software ImageJ (NIH, USA), the length between the fluorescence bands formed by the deposition of tetracycline in the growth plate and the bone tissue was measured, and Student's t-test and ANOVA test for comparison with a control group were performed in order to determine the growth effect.

<1-3> Administration of *Hordeum vulgare* Extract

The *Hordeum vulgare* extract prepared in Example 1 was administered after having been dissolved in a concentration of 30 mg/kg in type II distilled water in a volume of 1.0 ml per 100 g of rat weight, and as a control group, the same volume of type II distilled water was administered. The *Hordeum vulgare* extract was orally administered two times a day for a total of four days, starting from 2 days before the administration of tetracycline until the test termination day.

<1-4> Administration of Positive Control Group

Based on the reports of increasing the bone growth using recombinant human growth hormone (Isgaard J, Nilsson A, Lindahl A, Jansson J O, and Isaksson O G: Effects of local administration of GH and IGF-1 on longitudinal bone growth in rats. Am J Physiol. 250:E367-72, 1986), as a positive control group, 20 μg/kg of a recombinant human growth hormone (rhGH; LG Lifescience, Eutropin®) was administered at a volume of 0.1 ml per 100 g of rat weight. For the positive control group, the recombinant human growth hormone was subcutaneously injected once a day for a total of 4 days, starting from 2 days before the administration of tetracycline until the test termination day, and for the other group, distilled water was subcutaneously injected.

<1-5> Evaluation of Longitudinal Bone Growth Effect of *Hordeum vulgare* Extract Based on the results of direct measurement of the longitudinal bone growth through the tetracycline staining method, the longitudinal bone growth rate of the positive control group was found to be 360.1±35.8 μm/day (n=5), which is 6.6% higher than 337.8±30.0 μm/day (n=6) in the normal control group, but the difference was not significant.

Figure 2:
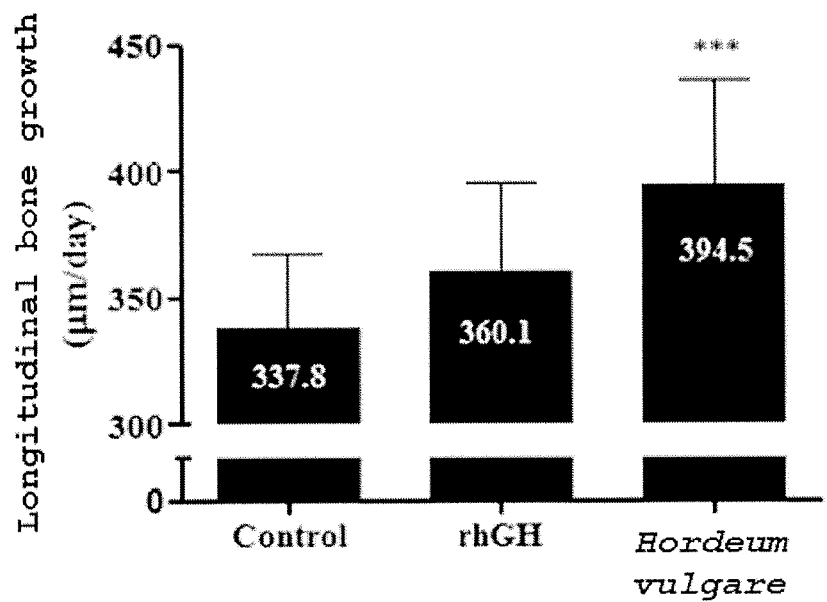
FIG. 2 is a graph illustrating the extent of longitudinal bone growth in rats.

In the group administered with 30 mg/kg of *Hordeum vulgare* extract (p.o.), the longitudinal bone growth rate was 394.5±41.38 μm/day (n=6) and thus a significant bone growth effect was exhibited compared to the normal control group (16.8%, p<0.001) (FIG. 2). Thus, when the *Hordeum vulgare* extract was administered, the longitudinal bone growth effect could be confirmed to remarkably increase.

The test results are summarized in Table 1 below.

TABLE 1

| | Dose (Administration route) | Longitudinal bone growth rate (%) |
|---|---|---|
| Control group | — | — |
| Positive control group | 20 μg/kg (s.c.) | 6.6% |
| *Hordeum vulgare* extract | 30 mg/kg (p.o.) | 16.8% |

INDUSTRIAL APPLICABILITY

According to the present invention, a composition comprising *Hordeum vulgare* extract as an active ingredient can prevent, ameliorate or treat growth disorder.

The invention claimed is:

1. A method for promoting longitudinal bone growth of an animal in need thereof, comprising administering a feed composition comprising an effective amount of a *Hordeum vulgare* extract to the animal.

2. A method of promoting longitudinal bone growth of a subject in need thereof, comprising administering a pharmaceutical composition comprising an effective amount of a *Hordeum vulgare* extract to the subject.

3. The method of claim 2, wherein the *Hordeum vulgare* extract is extracted in water, a C1-C4 alcohol, or a mixture thereof.

4. The method of claim 2, wherein the pharmaceutical composition is orally administered.

5. The method of claim 1, wherein the *Hordeum vulgare* extract is extracted in water, a C1-C4 alcohol, or a mixture thereof.

6. The method of claim 1, wherein the feed composition further comprises an additional active ingredient having an effect of treating a growth disorder.

7. The method of claim 2, wherein the pharmaceutical composition further comprises an additional active ingredient having an effect of treating a growth disorder.

\* \* \* \* \*